United States Patent [19]
Maynard

[11] Patent Number: 6,072,154
[45] Date of Patent: Jun. 6, 2000

[54] SELECTIVELY ACTIVATED SHAPE MEMORY DEVICE

[75] Inventor: Ronald S. Maynard, Sunnyvale, Calif.

[73] Assignee: Medtronic, Inc., Minneapolis, Minn.

[21] Appl. No.: 08/774,565

[22] Filed: Dec. 31, 1996

Related U.S. Application Data

[63] Continuation-in-part of application No. 08/708,586, Sep. 5, 1996.

[51] Int. Cl.[7] .................................................. H05B 1/00
[52] U.S. Cl. ............................ 219/209; 219/548; 604/53; 604/95; 604/281
[58] Field of Search .................................. 604/53, 95, 93, 604/114, 281; 128/657, 658, 786; 219/209, 201, 522, 528, 533, 534, 548, 552, 553

[56] References Cited

U.S. PATENT DOCUMENTS

| | | | |
|---|---|---|---|
| 4,337,090 | 6/1982 | Harrison | 148/402 |
| 4,524,343 | 6/1985 | Yaeger et al. | 60/527 |
| 4,533,411 | 8/1985 | Melton | 148/402 |
| 4,543,090 | 9/1985 | McCoy | 604/95 |
| 4,553,393 | 11/1985 | Ruoff | 60/528 |
| 4,559,512 | 12/1985 | Yaeger et al. | 337/140 |
| 4,565,589 | 1/1986 | Harrison | 148/402 |
| 4,601,705 | 7/1986 | McCoy | 604/95 |
| 4,631,094 | 12/1986 | Simpson et al. | 148/11.5 |
| 4,665,906 | 5/1987 | Jervis | 128/92 |
| 4,700,541 | 10/1987 | Gabriel et al. | 60/528 |
| 4,753,223 | 6/1988 | Bremer | 128/4 |
| 4,758,222 | 7/1988 | McCoy | 604/95 |
| 4,770,725 | 9/1988 | Simpson et al. | 148/402 |
| 4,776,541 | 10/1988 | Maynard | 244/165 |
| 4,777,799 | 10/1988 | McCoy et al. | 60/528 |
| 4,790,624 | 12/1988 | Van Hoye et al. | 350/96.26 |
| 4,884,557 | 12/1989 | Takehana et al. | 128/4 |
| 4,918,919 | 4/1990 | McCoy et al. | 60/528 |
| 4,990,883 | 2/1991 | Escobar et al. | 337/357 |
| 4,994,727 | 2/1991 | McCoy | 604/95 |
| 5,055,101 | 10/1991 | McCoy | 604/95 |
| 5,061,914 | 10/1991 | Busch et al. | 337/140 |
| 5,067,957 | 11/1991 | Jervis | 606/108 |
| 5,078,684 | 1/1992 | Yasuda | 604/95 |
| 5,090,956 | 2/1992 | McCoy | 604/95 |
| 5,114,402 | 5/1992 | McCoy | 604/95 |
| 5,135,517 | 8/1992 | McCoy | 604/281 |
| 5,165,897 | 11/1992 | Johnson | 434/113 |
| 5,176,544 | 1/1993 | Abujudom, II et al. | 439/878 |
| 5,188,111 | 2/1993 | Yates et al. | 128/657 |
| 5,190,546 | 3/1993 | Jervis | 606/78 |
| 5,229,211 | 7/1993 | Murayama et al. | 428/424.4 |
| 5,254,130 | 10/1993 | Poncet et al. | 606/206 |
| 5,279,559 | 1/1994 | Barr | 604/95 |
| 5,309,717 | 5/1994 | Minch | 60/527 |
| 5,334,168 | 8/1994 | Hemmer | 604/281 |
| 5,335,498 | 8/1994 | Komatsu et al. | 60/528 |
| 5,345,937 | 9/1994 | Middleman et al. | 128/657 |
| 5,405,337 | 4/1995 | Maynard | 602/128 |
| 5,481,184 | 1/1996 | Jacobsen | 324/106 |
| 5,482,029 | 1/1996 | Sekiguchi et al. | 600/109 |
| 5,531,685 | 7/1996 | Hemmer et al. | 604/95 |
| 5,556,370 | 9/1996 | Maynard | 600/142 |
| 5,624,380 | 4/1997 | Takayama et al. | 600/146 |
| 5,662,621 | 9/1997 | Lafontaine | 604/281 |

FOREIGN PATENT DOCUMENTS

| | | | |
|---|---|---|---|
| 61-185082 | 8/1986 | Japan | H02N 10/00 |
| 61-190177 | 8/1986 | Japan | F03G 7/06 |
| 3-5128 | 1/1991 | Japan | B29C 67/18 |
| 7-75355 | 3/1995 | Japan | H02N 10/00 |
| 7-247954 | 9/1995 | Japan | F03G 7/06 |
| 1696298 A1 | 7/1991 | Russian Federation | B25J 11/00 |
| 1696298 | 12/1991 | U.S.S.R. | |
| WO95/34189 | 12/1995 | WIPO | H05B 3/00 |

*Primary Examiner*—Teresa Walberg
*Assistant Examiner*—Shawntina Fuqua
*Attorney, Agent, or Firm*—Reed A. Duthler; Harold R. Patton

[57] ABSTRACT

A shape memory device includes a shape memory alloy member configured to have at least a portion of the shape memory alloy member be selectively activated. A heating device is coupled to the member and configured to provide heat to a selected section of the member and activate at least a portion of the selected section.

29 Claims, 13 Drawing Sheets

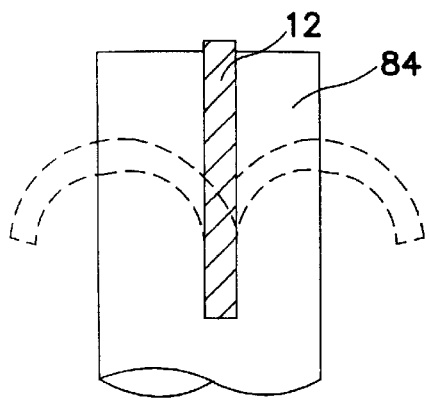
FIG. 20
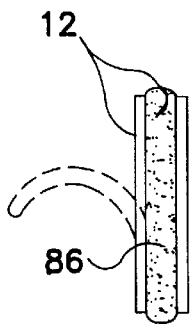
FIG. 21
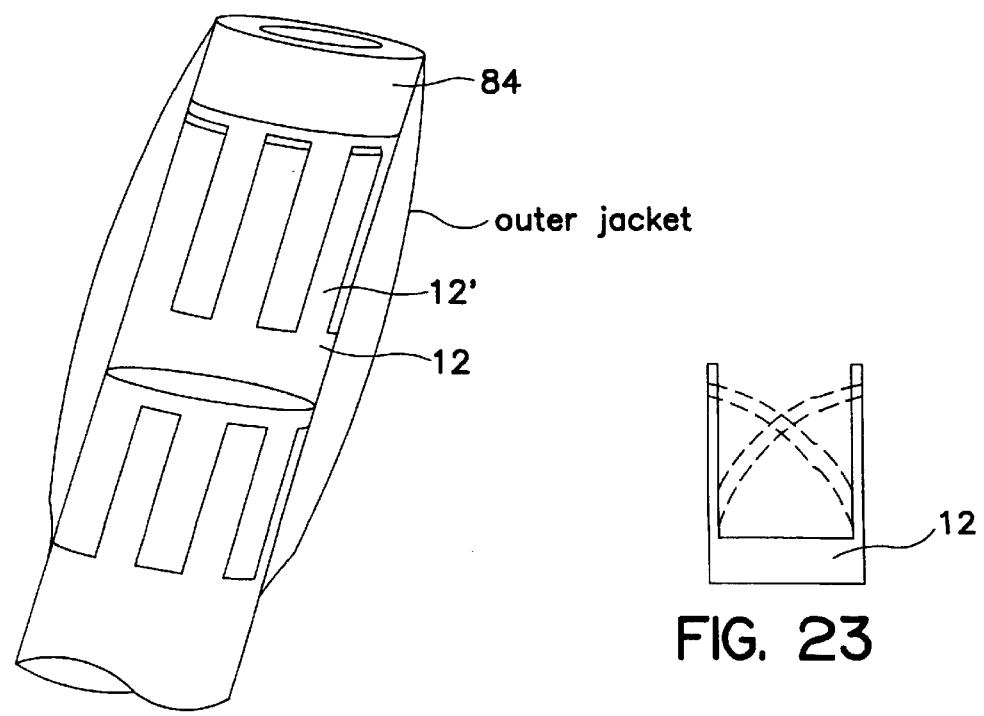
FIG. 22
FIG. 23

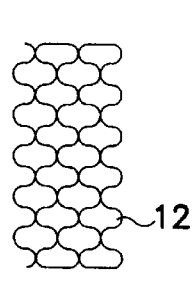
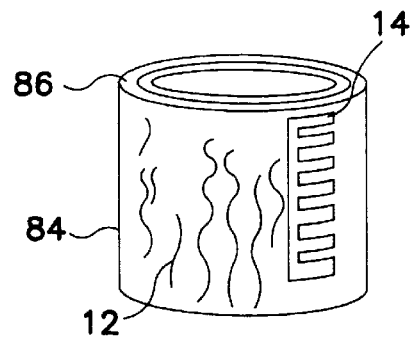
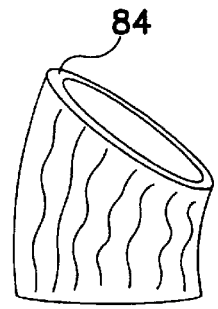
FIG. 29  FIG. 30  FIG. 31
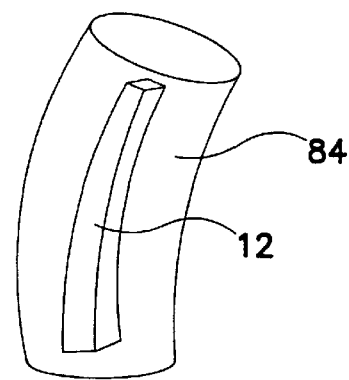
FIG. 28

SELECTIVELY ACTIVATED SHAPE MEMORY DEVICE

CROSS-REFERENCE TO RELATED APPLICATIONS

This invention is a continuation-in-part of U.S. patent application Ser. No. 08/708,586, filed Sep. 5, 1996, entitled "DISTRIBUTED ACTUATOR FOR A TWO-DIMENSIONAL SHAPE MEMORY ALLOY", incorporated herein by reference.

BACKGROUND

1. Field of the Invention

This application relates to shape memory devices, and more particularly to a spatially addressable shape memory device.

2. Description of Related Art

Materials which change their shape in response to external physical parameters are known and appreciated in many areas of technology. Shape memory alloys (hereafter "SMA") is a material that undergoes a micro-structural transformation from a martensitic phase at a low temperature to an austenitic phase at a high temperature. In the martensitic phase an SMA exhibits low stiffness and may be readily deformed up to 8% total strain in any direction without adversely affecting its memory properties. When heated to an activation temperature, the SMA becomes two to three times stiffer as it approaches its austenitic state. At the higher temperature, the SMA attempts to reorganize itself on the atomic level to accommodate a previously imprinted or "memorized" shape. When the SMA cools it returns to its soft martensitic state.

A shape may be trained into an SMA by heating it well beyond its activation temperature to its annealing temperature and holding it there for a period of time. For a TiNi SMA system, the annealing program consists of geometrically constraining the specimen, and heating it to approximately 520 degrees C. for fifteen minutes. Usually, functionally is enhanced by leaving in a certain amount of cold working by abbreviating the anneal cycle.

U.S. Pat. No. 4,543,090 (hereafter the "'090 Patent") discloses a catheter with two distinct SMA actuators. One actuator assumes a predetermined shape when heated to a predetermined temperature. The two actuators are coupled to each other with a coupling device so that when one of the actuator moves to its predetermined shape a force is applied to move the second actuator in the direction of the first actuator. Each actuator is only able to move to a single predetermined shape. The actuators do not include a heating device with at least two micro-fabricated address lines. The limitations of the '090 Patent are also found in U.S. Pat. No. 4,601,705.

It would be desirable to provide a shape memory alloy device that has a sheet of shape memory alloy where a section of the sheet can be selectably activated.

SUMMARY

An object of the present invention is to provide a shape memory device that is selectably activated.

Another object of the present invention is to provide a shape memory device that is activated to more than a single predetermined shape.

Still another object of the present invention is to provide a shape memory device with a shape memory alloy and a heating device that includes at least one micro-fabricated conductive path.

Another object of the present invention is to provide a shape memory device where an activation of at least a portion of the shape memory device provides a variable Young's modulus of at least a portion of the shape memory device.

Yet another object of the present invention is to provide a medical device that includes a shape memory alloy actuator that is selectably activated to a selected site of the actuator.

Still a further object of the present invention is to provide a medical device that includes a sheet of shape memory alloy that is activated at a selected site of the sheet and the sheet is coupled to a catheter body.

Another object of the present invention is to provide a medical device with a single shape memory alloy actuator.

A further object of the present invention is to provide a shape memory device with a plurality of independently addressable actuators.

Yet a further object of the present invention is to provide a thermally activated apparatus that includes a temperature-activated actuator configured to move to a plurality of different predetermined shapes.

These and other objects of the invention are achieved in a shape memory device that includes a shape memory alloy member configured to have at least a portion of the shape memory alloy member be selectively activated. A heating device is coupled to the member and configured to provide heat to a selected section of the member and activate at least a portion of the selected section.

In one embodiment of the invention, a shape memory device includes a sheet of a shape memory alloy. The sheet is selectably activated to a selected site of the sheet and includes at least two independently actuateable elongated members. A heating device is positioned adjacent to or on a surface of the sheet to provide heat to a selected section of the sheet and create a bending force within at least a portion of the selected section. The heating device includes at least one micro-fabricated conductive path.

In another embodiment of the invention, a medical device includes an elongated device at least partially made of a shape memory alloy member configured to be selectably activated at a selected site of the member. A heating device is coupled to the member and configured to provide heat to a selected section of the member and activate at least a portion of the selected section.

In yet another embodiment of the invention, a catheter is provided with an elongated device that includes a distal end and proximal end. A shape memory alloy member is configured to be selectably activated at a selected site of the member. The member is coupled to the elongated device. A heating device is coupled to the member and configured to provide heat to a selected section of the member and activate at least a portion of the selected section.

In still another embodiment of the invention, a shape memory device includes a shape memory alloy member that is configured to be selectably activated at a selected site of the member. The member has at least two independently activated elongated portions. A heating device is coupled to the member and configured to provide heat to a selected section of the member and activate at least a portion of the selected section.

In another embodiment of the invention, a thermally activated apparatus includes a temperature-activated actuator. The actuator is configured to move to a plurality of predetermined shapes. A heating device is configured to deliver thermal energy to at least a selected portion of the actuator.

In still a further embodiment of the invention, a medical device includes an elongated member with a proximal portion and a distal portion configured to be inserted into a body. An electrically-activated actuator is coupled to the elongated member. The actuator is configured to move to a plurality of predetermined shapes. An electrical energy source is coupled to the electrically-activated actuator and configured to deliver energy to at least a selected portion of the actuator.

In yet another embodiment of the invention, a thermally activated apparatus includes an electrically-activated actuator coupled to an elongated member. The actuator is configured to move to a plurality of predetermined shapes. An electrical energy source is coupled to the electrically-activated actuator and configured to deliver energy to at least a selected portion of the actuator.

In various embodiments of the invention, an activation of at least a portion of the selected section of the actuator provides a variable Young's modulus of at least a portion of the actuator. The heating device can include a micro-fabricated conductive path. The actuator can be made of a continuous sheet of a shape memory alloy, a sheet of a shape memory alloy which includes perforations, or a plurality of interconnected separate shape memory alloy actuators. The actuator can have a three-dimensional geometry, a wire-like geometry, a tube-like structure and the like. A micro-fabricated circuit, a micro-fabricated sensor, or a micro-fabricated transducer can be coupled to the heating device.

The medical device of the present invention can be an endoscope, a catheter, a cannula, an introducer, a laparoscope, a trocar and a catheter. The operation mode of the shape memory alloy of the medical device is achieved by, (i) one-way shape memory effect acting on an elastic body such as a catheter which provides a return force, (ii) using one-way shape memory effect and directly applying a restoring force with a superelastic shape memory alloy spring, an elastomeric spring and the like, or (iii) utilizing a two-way shape memory effect.

BRIEF DESCRIPTION OF THE DRAWINGS

FIG. 20 is a cross section of a catheter with the actuator illustrated in FIG. 2.

FIG. 21 is a cross section view of two actuators illustrated in FIG. 2 with a thermally insulating elastomer.

FIG. 22 illustrates the actuator of FIG. 2 coupled to a catheter.

FIG. 23 illustrates an actuation path of the actuator of FIG. 2 in a push embodiment.

FIG. 28 is a cross section of an a catheter without a lumen and the actuator of FIG. 2 positioned in the catheter.

FIG. 29 is a perspective view of a mesh configuration of the actuator of the present invention.

FIG. 30 illustrates the actuator of FIG. 29 coupled to a catheter.

FIG. 31 illustrates the result of applying heat to selected sections of the mesh of FIG. 30.

DESCRIPTION

Figure 1:
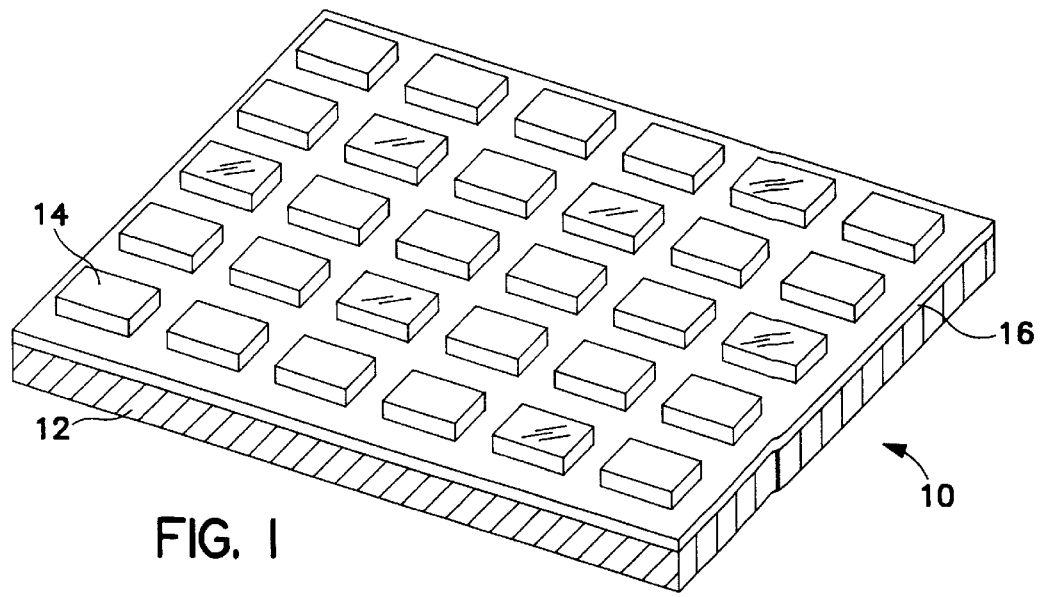
FIG. 1 is an isometric view of a deactivated two-dimensional sheet according to the invention.

One embodiment of the present invention is a shape memory device that includes a shape memory alloy member configured to have at least a portion of the shape memory alloy member selectively activated. A heating device is coupled to the member and configured to provide heat to a selected section of the member and activate at least a portion of the selected section.

In another embodiment of the present invention, a shape memory device includes a sheet of a shape memory alloy. The sheet is selectably activated to a selected site of the sheet and includes at least two independently actuateable elongated members. A heating device is positioned adjacent to or on a surface of the sheet to provide heat to a selected section of the sheet and create a bending force within at least a portion of the selected section. The heating device includes at least one micro-fabricated conductive path.

In still another embodiment of the invention, a medical device includes an elongated device at least partially made of a shape memory alloy member configured to be selectably activated at a selected site of the member. A heating device is coupled to the member and configured to provide heat to a selected section of the member and activate at least a portion of the selected section.

In yet another embodiment of the invention, a medical device is an elongated device that includes a distal end and proximal end. A shape memory alloy member is configured to be selectably activated at a selected site of the member. The member is coupled to the elongated device. A heating device is coupled to the member and configured to provide heat to a selected section of the member and activate at least a portion of the selected section.

In still another embodiment of the invention, a shape memory device includes a shape memory alloy member that is configured to be selectably activated at a selected site of the member. The member has at least two independently activated elongated portions. A heating device is coupled to the member and configured to provide heat to a selected section of the member and activate at least a portion of the selected section.

In another embodiment of the invention, a thermally activated apparatus includes a temperature-activated actuator. The actuator is configured to move to a plurality of predetermined shapes. A heating device is configured to deliver thermal energy to at least a selected portion of the actuator.

In still a further embodiment of the invention, a medical device includes an elongated member with a proximal portion and a distal portion configured to be inserted into a body. An electrically-activated actuator is coupled to the elongated member. The actuator is configured to move to a plurality of predetermined shapes. An electrical energy source is configured to be coupled to the electrically-activated actuator and deliver energy to at least a selected portion of the actuator.

In yet another embodiment of the invention, a thermally activated apparatus includes an electrically-activated actuator coupled to an elongated member. The actuator is configured to move to a plurality of predetermined shapes. An electrical energy source is coupled to the electrically-activated actuator and configured to deliver energy to at least a selected portion of the actuator.

In various embodiments of the invention, an activation of at least a portion of the selected section of the actuator provides a variable Young's modulus of at least a portion of the actuator. The heating device can include a micro-fabricated conductive path. The actuator can be made of a continuous sheet of a shape memory alloy, a sheet of a shape memory alloy which includes perforations, or a plurality of interconnected separate shape memory alloy actuators. The actuator can have a three-dimensional geometry, a wire-like geometry, a tube-like structure and the like. A micro-fabricated circuit, a micro-fabricated sensor, or a micro-fabricated transducer can be coupled to the heating device.

The medical device of the present invention can be an endoscope, a catheter, a cannula, an introducer, a laparoscope, a trocar, surgical intervention devices and the like. The operation mode of the shape memory alloy device is achieved by, (i) one-way shape memory effect acting on an elastic body such as a catheter which provides a return force, (ii) using one-way shape memory effect and directly applying a restoring force with a superelastic shape memory alloy spring, an elastomeric spring and the like, or (iii) utilizing a two-way shape memory effect.

Referring now to FIG. 1, a shape memory device 10 includes a sheet of a shape memory alloy 12 that is made entirely of a SMA. Most common examples include TiNi alloys and CuZnAl alloys. Other alloys and shape memory polymers can also be used. The ratio of the thickness of sheet 12 to the lateral extent of a heating element 14 should be preferably as small as possible, while still capable of maintaining the integrity of sheet 12. Shaped memory device 10 is configured to be selectably activated to a selected site of sheet 12. This provides for the movement, or actuation, of different sections of sheet 12. By heating portions of sheet 12, spatially complex bending forces are generated within sheet 12. Heating elements 14 provide thermal energy to sheet 12 directly, ohmicaly, and from a number of different energy sources including but not limited to electromagnetic, microwave, resistive heating, ultrasound and RF. Heating elements 14 are electrically isolated from sheet 12, from each other and from the local environment.

SMA sheet 12 can be flexible and produced by a variety of common machining methods; such as rolling of thin foils from wire or thin plate stock, sectioning thin wafers from bar stock, or like methods. Wafers of SMA material may be sliced from bar stock using a conventional band saw, a cold saw, an annular diamond wet saw, or electro-discharge machining (EDM) or like methods. The resulting wafers or foils can be heat treated to a flat condition and precision-ground to any desired thickness. SMA bulk properties are assured as the material is obtained directly from bulk. The SMA material contained in sheet 12 can be thermally pre-trained prior to assembly or left untrained. The choice depends on the eventual application.

A plurality of heating elements 14 are positioned on top of SMA sheet 12 and insulated from sheet 12 by an electrically insulating layer 16. It is most convenient to laminate or otherwise deposit electrically insulating layer 16 on sheet 12. Electrically insulating layer 16 prevents current leakage between heating elements 14 and electrically conducting sheet 12. Electrically insulating layer 16 is also preferably is a good thermal conductor. Preferred insulating materials include polyimide elastomers, plastics, silicon nitride $Si_xN_y$, and the like. The thickness of electrically insulating layer 16 should be small in relation to its lateral extent. For example, electrically insulating layer 16 may be a 2000 Å silicon nitride layer to ensure adequate thermal coupling, and to ensure thermal conductivity between heating elements 14 and sheet 12.

In the embodiment of FIG. 1, heating elements 14 are in the form of thin film resistors. Most preferably, heating elements 14 are ohmic heaters or other similar devices capable of converting electrical current to thermal energy. They can be comprised of any conventional resistive material such as TiW or TaO. Conveniently, the resistive material is first deposited and patterned on layer 16 by well known VLSI or micro-machining techniques. Heating elements 14 are patterned or otherwise formed according to well-known photolithographic procedures such as the additive process of lift off or the subtractive process of dry or wet etching.

Shape memory device 10 can be operated in either open loop or closed loop mode. In open loop mode, a predetermined path of travel is programmed in a microprocessor. The microprocessor then provides output signals to the address decode circuitry which is integrated in VLSI on a proximal portion of shape memory device 10. The predetermined travel path is then mapped into latch registers or logic gates in the address decode circuitry in accordance with techniques which are well known. The address decode circuitry then activates selected portions of shape memory device 10.

In the closed loop mode, the position signal received from each position or bend sensor is utilized by an adaptive feedback control method that centers shape memory device 10 on a path of travel. The microprocessor is able to determine the angular displacement and thus the position of shape memory device 10. From this, the overall position of shape memory device 10 can be determined for given positional intervals.

Angular displacement of shape memory device 10 may also be determined by observing the current and/or voltage delivered to each heater element 14. From the current and voltage information an instantaneous local resistance may be inferred. Conventional means are provided for sensing the voltages at different nodes. The voltage information is provided to microprocessor over a communication path.

A look-up table of temperature/resistance relationships is embodied in the microprocessor. The look-up table is optimized for each shape memory device 10 formulation in order to provide a narrow hysterisis loop. In the look-up table, the microprocessor then correlates each resistance value with a temperature and consequently can determine the activation state and thus, the angular displacement and position of shape memory device 10. A position mapping means in the microprocessor comprises a means for establishing a reference array comprising a locus of angular positions for shape memory device 10. This in turn defines a path of travel for shape memory device 10. Once a locus of angular positions is stored, the memorized travel path is repeatable with extreme speed. Accordingly a catheter coupled to shape memory device 10 can instantly reverse both its direction and activation sequence so that it precisely retraces even the most complex path of travel. The position mapping means may store one or more paths of travel in memory.

Figure 3:
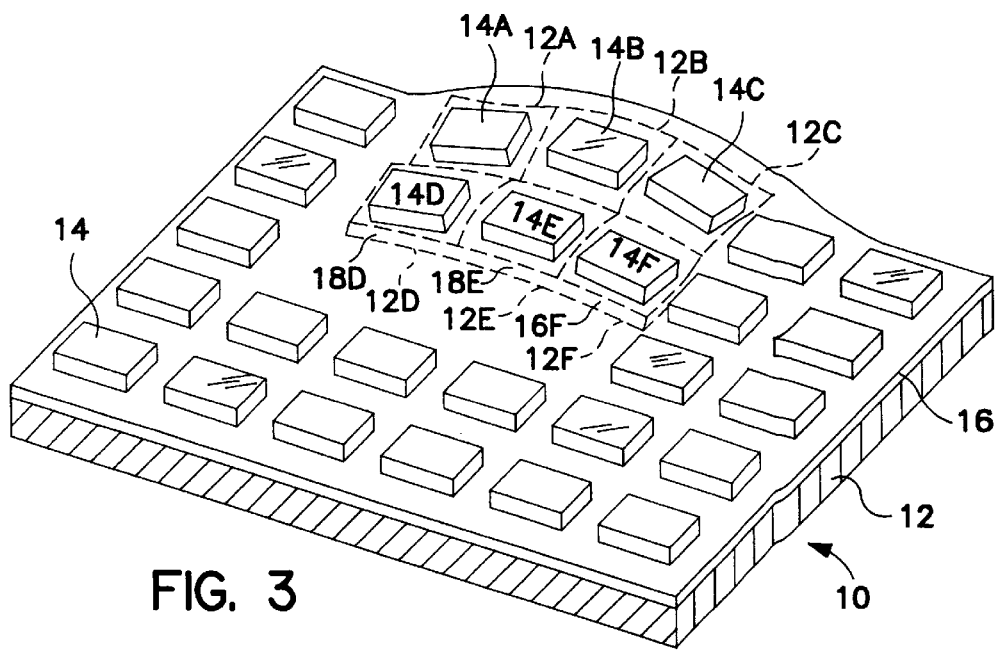
FIG. 3 is an isometric view of the two-dimensional sheet of FIG. 1 in the activated state.
Figure 2:
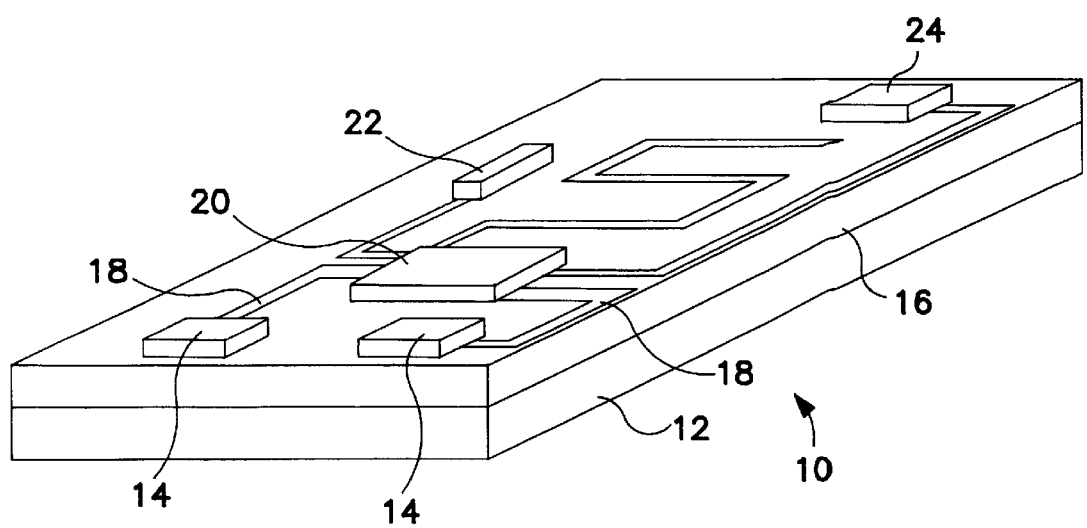
FIG. 2 is a perspective view of the two-dimensional sheet of FIG. 1 illustrating micro-fabricated structures.

As shown in FIG. 2, heating elements 14 may include at least one micro-fabricated conductive path 18 coupled to a single current source. A single current source can deliver current to any number of different heating elements 14 by the use of multiplexing power transistors. A transistor may be pulse width modulated to deliver a metered amount of power. Optionally included are a micro-fabricated circuit 20, a micro-fabricated sensor 22 and a micro-fabricated transducer 24. Micro-fabricated sensors include but are not limited to pressure, temperature, electrosonic, voltage potential, chemical, chemical potential and an electromagnetic sensor. Micro-fabricated transducers include temperature, electrosonic, voltage potential and an electromagnetic transducer. FIG. 3 shows a particular case wherein six heating elements 14, labeled as 14A–14F, are providing heat. In the case where shaped memory device 10 is limitedly constrained by its environment heat traverses section 16A–16F of insulating layer 16 and causes adjacent portions 12A–12F of SMA sheet 12 to reach activation threshold. As a result, portions of 12A–12F are activated and assume a well-defined shape and in the process provide useful activation forces. As shown, the local deformation is upward convex. Once portions 12A–12F convert to a predominantly austenitic composition and assume their pre-determined shapes, the areas of sheet 12 surrounding those portions are characterized by martensitic composition and deform in accordance with conventional laws of continium mechanics. In the simple case of FIG. 3, the remainder of sheet 12 remains flat or otherwise undisturbed from its initial state.

Figure 4:
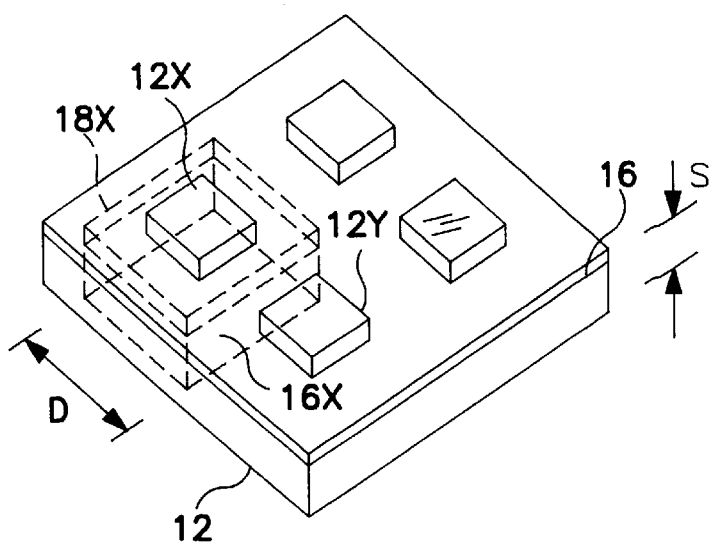
FIG. 4 is an isometric view of a portion of the two-dimensional sheet of FIG. 1.

In FIG. 4 the thickness of sheet 12 is labeled by S. For clarity, a particular heating element 14X has been selected to explain the details of the invention. Heating element 14X has associated with it an adjacent portion 12X of sheet 12. As shown, heating element 14X has associated with it a section 16X of electrically insulating layer 16 as well. Portion 12X is located directly underneath heating element 14X. The width of portion 12X is denoted by D. As shown, heating element 14X provides heat to portion 12X exclusively. Heat propagates through section 16X and into section 12X which represents a localized portion of sheet 12.

Figure 4A:
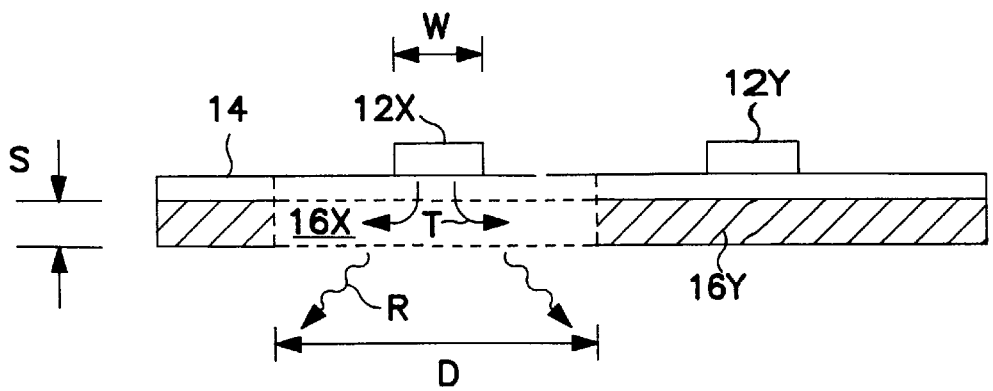
FIG. 4(a) is a cross section of the portion of the two-dimensional of FIG. 4.

The principles behind the heating process and the shape assumed by adjacent portions 12 are best illustrated in FIG. 4A with a single heating element 14X. For clarity, the predetermined shape assumed by adjacent portion 12X upon heating has not been shown. The heat generated by element 14X, whose width is indicated by W, passes along arrows through insulating layer 16. In particular, the thermal energy traverses section 16X of layer 16. Layer 16 is proportionally very thin compared to the lateral dimensions, and thus section 16X readily transfers the heat to sheet 12. Once in sheet 12 the heat propagates throughout adjacent portion 12X. Due to a relatively thin section S heat conductive in the lateral direction is far less than in the normal direction. During a typical operation cycle the applied heat energy remains localized.

Figure 4B:
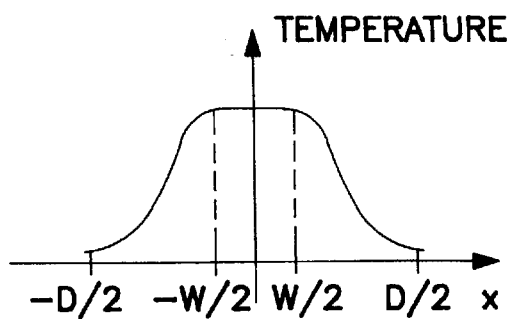
FIG. 4(b) is a graph of the temperature distribution in the portion of FIG. 4(a).

Graph 4B represents temperature distributions at an arbitrary fixed depth below heater 14X. The graph in FIG. 4B shows the temperature distribution laterally, in the X direction, inside portion 12X. Directly under element 14X the temperature remains at a maximum, as indicated by the flat portion of the curve from −W/2 to +W/2. In other words, the heat delivered to portion 12X does not propagate to other portions 12, e.g., portion 12Y. Instead, the heat radiates along arrows R out of sheet 12 before reaching other portions 12.

Figure 5:
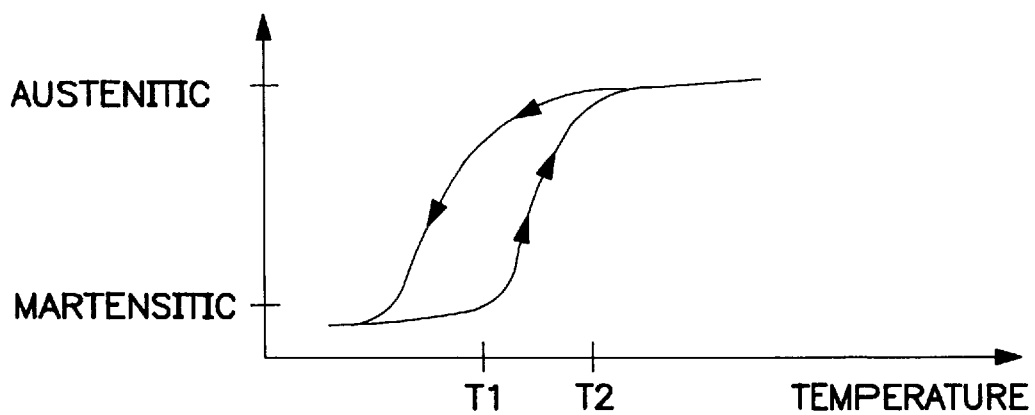
FIG. 5 is a hysterisis curve of the transition between the martensitic and austenitic states as a function of temperature.

As already mentioned, the shape of adjacent portions 12 depends on the pre-trained shape of the SMA or sheet 12 in those regions. Also, the shape depends on the temperature maintained in portions 12. Full conformity to the pre-trained shape is achieved when the temperature in portions 12 is equal or higher than the critical temperature at which the SMA material attains the austenitic state. This is best shown in the graph of FIG. 5. At temperatures below $T_1$ the SMA material remains pliable, as dictated by the martensitic properties. Therefore, portions 12 maintained at or below $T_1$ will conform to the shape imparted to them by the surroundings. The transition to the austenitic state occurs between temperatures $T_1$ and $T_2$. When portions 12 are kept in this temperature range they will assume an intermediate shape between the relaxed and pre-trained forms. Careful thermal regulation thus allows one to vary the shape of any portions 12 of sheet 12 in a continuous manner.

The overall structure of sheet 12 where heating elements 14 are mounted directly on sheet 12 with only layer 16 interposed between them is very simple. The assembly process is straightforward and low-cost.

Figure 6:
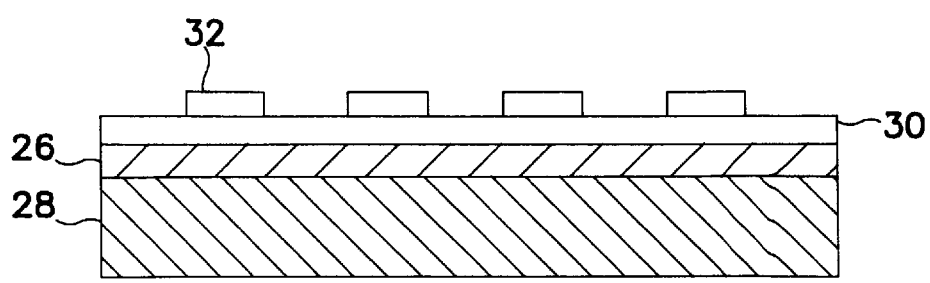
FIG. 6 is a cross section of a two-dimensional sheet with an insulating layer and a coating layer.

Another embodiment of the invention is shown in FIG. 6. Here a two-dimensional sheet 26 of SMA material is placed on a coating layer 28. In this case, layer 28 is sufficiently thick to provide mechanical stability during processing.

A thin insulating layer 30 is positioned on top of sheet 26 to provide electrical insulation between heating elements 14 and sheet 26. Layer 30 is thin enough and has appropriate thermal properties to permit the free flow of heat from elements 14 to sheet 26. Additionally, layer 30 is also able to accommodate mechanical strains incurred during operation. In this embodiment the SMA material of sheet 26 is also electrically conducting (e.g., TiNi alloy or CuZnAl alloy).

Figure 7:
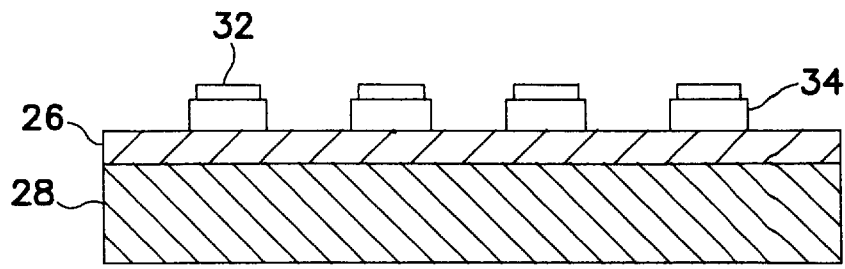
FIG. 7 is a cross section of a two-dimensional sheet with point-wise applied insulating layer and a coating layer.

FIG. 7 shows an embodiment where sheet 26 includes a coating layer and acts as a substrate. In this case layer 28 is chosen from materials which are chemically inert and stable to protect sheet 26 from adverse environmental conditions.

Electrical insulation between heating elements 32 and sheet 26 is provided by electrical insulation sections 34 that are deposited point-wise under elements 32. Such structures can be produced by initially applying a layer of insulating material and a layer of resistive material. Elements 32 and a corresponding electrical insulation sections 34 are fashioned by dry or wet aetching or another well-known processes.

Figure 8:
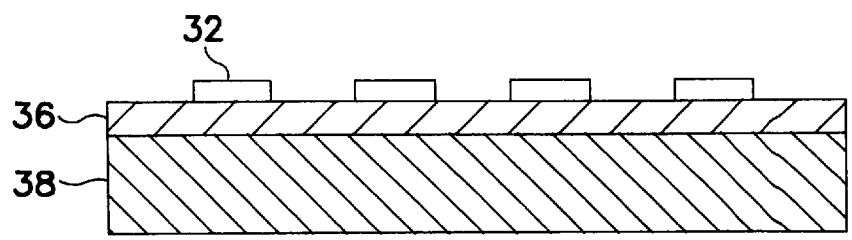
FIG. 8 is a cross section of a two-dimensional sheet with a coating layer.

FIG. 8 shows yet another embodiment in which a two-dimensional sheet 36 is made up of an electrically insulating SMA material. In this configuration no insulation is necessary. Consequently, heating elements 32 are mounted directly on sheet 36. A coating layer 38 functioning as substrate is once again provided to afford mechanical stability and resistance to adverse environmental conditions. It is preferable that layer 38 also be a good thermal conductor to aid in the dissipation of heat from sheet 36.

The embodiments of FIGS. 6–8 all operate in the manner set forth above. The modifications introduced are intended to aid one skilled in the art in selecting the appropriate structure given a set of technical requirements.

Figure 9:
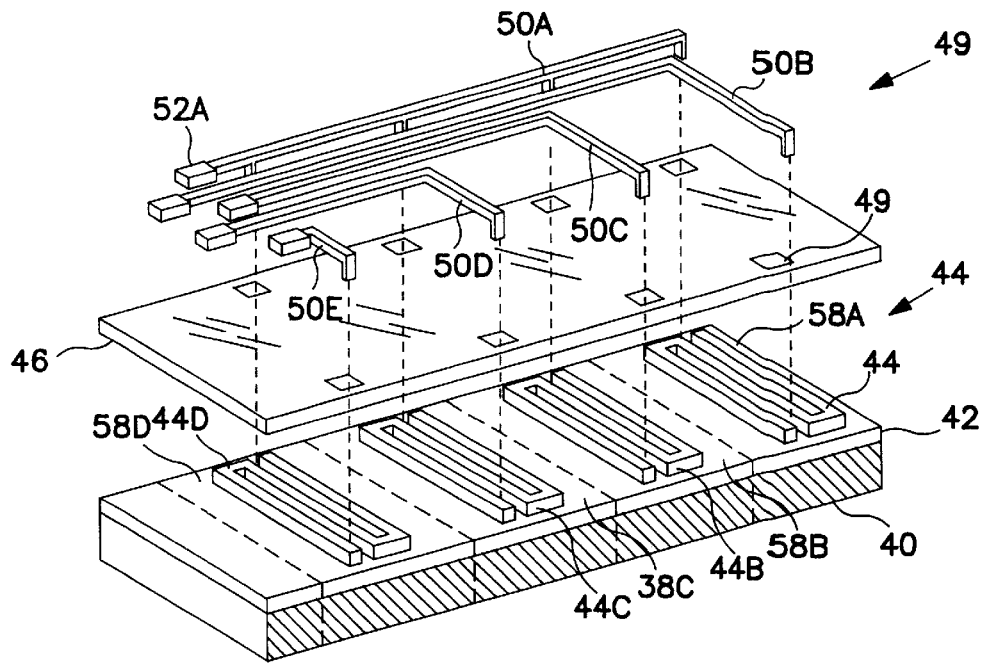
FIG. 9 is an exploded view illustrating the assembly of a two-dimensional sheet and the activation elements according to the invention.

One embodiment of the invention is shown in FIG. 9. A two-dimensional sheet 40 of an electrically conducting SMA material, preferably a NiTi alloy is coated with insulating layer 42. Preferably, layer 42 is made of $Si_xN_y$ or polyimide and is sufficiently thin to readily conduct heat.

Patterned heating elements 44 are located on layer 42. Elements 44 are obtained by sputtering and patterning TiW or TaO on top of layer 42. Heating elements 44 offer resistance of about a few hundred ohms. In the preferred embodiment elements 44 have a zig-zag shape when activated. This enables them to ensure better heat distribution in sheet 40 when active.

A second insulating layer 46 is provided on top of elements 44 and layer 42. Preferably, layer 46 is made of a flexible electrical insulation such as polyimide or an elastomer which may be spun coated onto elements 44 and layer 42. A number of through-holes 48 are opened in layer 46 to permit electrical contact with elements 44. Holes 48 are aligned with the terminal portions of elements 44.

A set of conductive paths 50 are patterned on top of layer 46. In one embodiment, conductive paths 50 are configured to deliver current to a selected portion of sheet 12 and provide ohmic heating to the selected portion of sheet 12. In another embodiment the ground return path is sheet 12 itself. Preferably, conduction lines 50 are made of a flexible and highly conductive material such as gold. Lines 50 can be defined by patterning or other suitable techniques. A common return line 50A is laid out to provide electrical contact with the left terminals of all elements 44. Return line 50A saves surface area of top of layer 46 and is desirable as long as all elements 44 are not addressed simultaneously on a continuous basis. If continuous activation is required, then an additional full width layer would be dedicated for the return path. Alternatively, conductive sheet 40 may itself provide the common ground return path for all heating elements 44. The other lines, 50B–50E are in electrical contact with the right terminals of elements 44 respectively.

External electrical connections are made to contact pads 52A–52E, corresponding to lines 50A–50E. For this purpose, pads 52A–52E are much thicker than lines 50A–50E. The actual electric connections are made with wire bonding or similar means.

Once the entire structure on sheet 40 is assembled, the SMA is "trained" by forcing sheet 40 to assume a resultant shape using well-known methods. For example, sheet 40 is formed on a mandrel and fixed in place with a clamp. The entire fixture is then placed in an annealing furnace, preferably purged with an inert gas, at approximately 450 degrees C. for about 30 minutes. Upon cooling the film is released from the mandrel. At this time sheet 40 is operationally ready.

Figure 10:
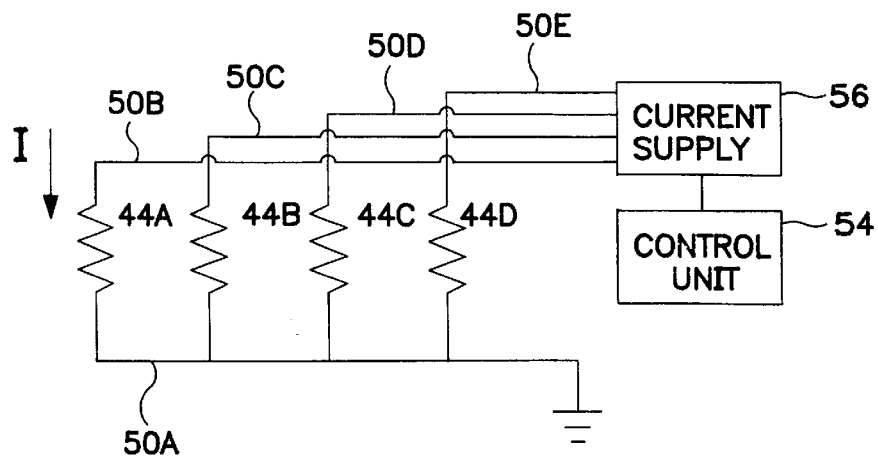
FIG. 10 is a diagram showing the equivalent circuit of the activation mechanism.

The electrical diagram showing the electrical connections of one embodiment is found in FIG. 10. A control unit 54 is connected to a current supply 56. Preferably, both unit 54 and supply 56 are located away from sheet 40. Unit 54 is preferably a micro-processor capable of selecting a desired combination of elements 44. Current supply 56 is preferably an adjustable source capable of delivering current to the selected combination of elements 44. Lines 50A–50E are connected directly to supply 56. Elements 44A–44D are shown as resistors. Return line 50A is grounded.

During operation control unit 54 selects a combination of elements 44 to be activated. It then sends a corresponding command to supply 56. Supply 56 responds by delivering current to elements 44 of the chosen combination. For example, elements 44A and 44D are chosen. Current is delivered to elements 44A and 44D and the corresponding adjacent portions 58A and 58D assume a well-defined shape. If the current is sufficiently large and the temperature maintained in adjacent portions 58A and 58D is above $T_2$ (see FIG. 5) then portions 58A and 58D will assume their pre-trained shape. If the temperature is between $T_1$ and $T_2$ portions 58A and 58D will assume an intermediate shape which is dependent on the path of travel about the hysterisis loop of FIG. 5. Because supply 56 is adjustable the proper current can be selected during operation and adjusted on an empirical basis. Consequently, the shape of portions 58A and 58D can be varied as necessary.

Figure 11:
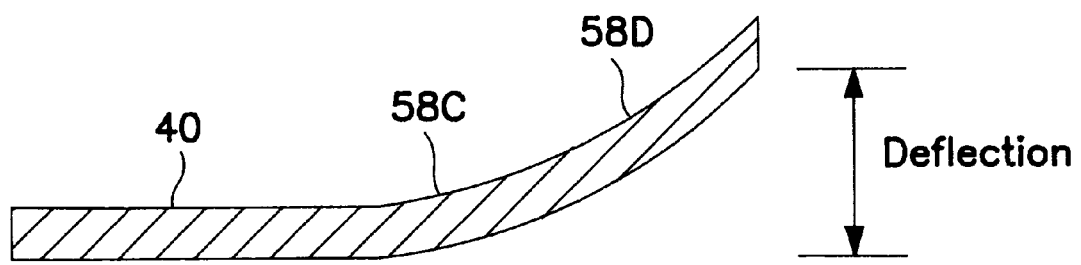
FIG. 11 is a side view illustrating the deflection of a two-dimensional sheet according to the invention.
Figure 12:
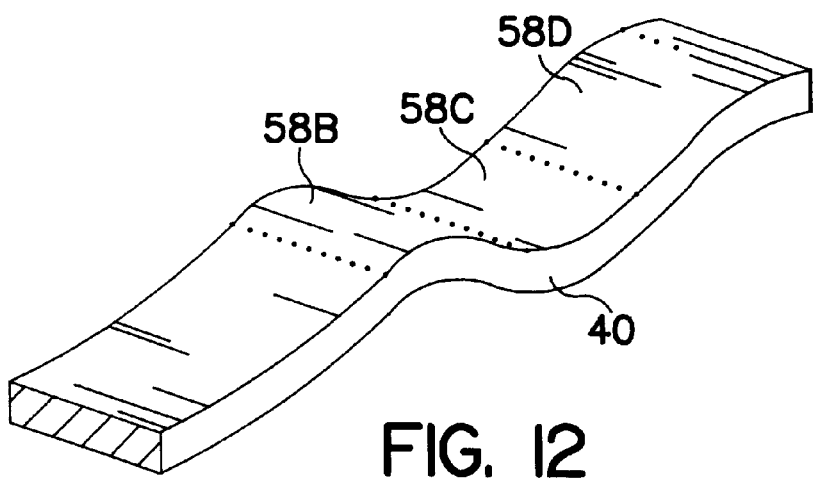
FIG. 12 is a perspective view illustrating a complex pre-trained shape of a sheet according to an aspect of the invention.

FIG. 11 illustrates the resultant shape of sheet 40 when adjacent portions 58C and 58D are selected. It is assumed that the SMA was pre-trained to curve upward along its entire length. Thus, together, deflections in portions 58C and 58D contribute to a much larger total deflection. FIG. 12 illustrates another possible resultant shape of layer 40 when sections 58B–58D are heated and the SMA was pre-trained to assume an S-shape. Throughout the description it is understood that the SMA of sheet 40 can be trained before or after assembly. Training before assembly can be preferable when working with materials which would be damaged if trained together with the SMA, e.g., due to the high annealing temperatures.

Figure 14:
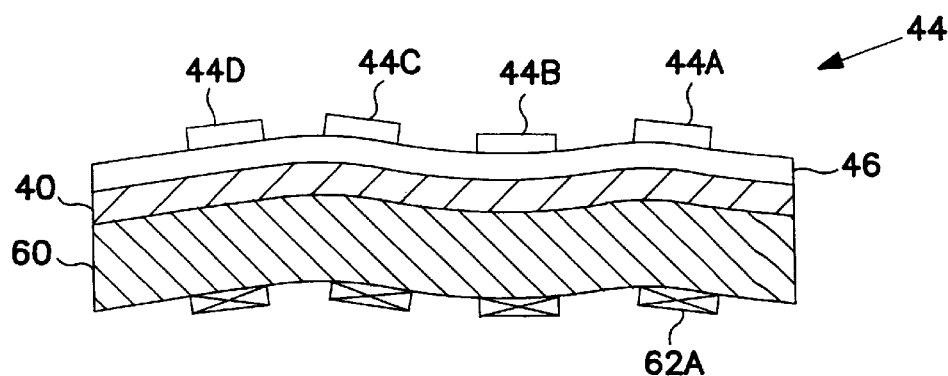
FIG. 14 is a cross sectional view of a two-dimensional sheet with deflection sensors.

In another embodiment, sheet 40 has a coating layer 60 as shown in FIG. 14. For better understanding, the deflections in sheet 40 have been indicated. Deflection sensors 62 are positioned on layer 60. Sensors 62 can be either angular deflections sensors, extension deflection sensors such as a strain gage, or bend sensors. A bend sensor is a type of strain gage configured for measuring bending strain and angular deflection. In this case sensors 62 have been placed in locations corresponding to those of elements 44. Depending on the geometry and application, different placement may be preferable.

Figure 13:
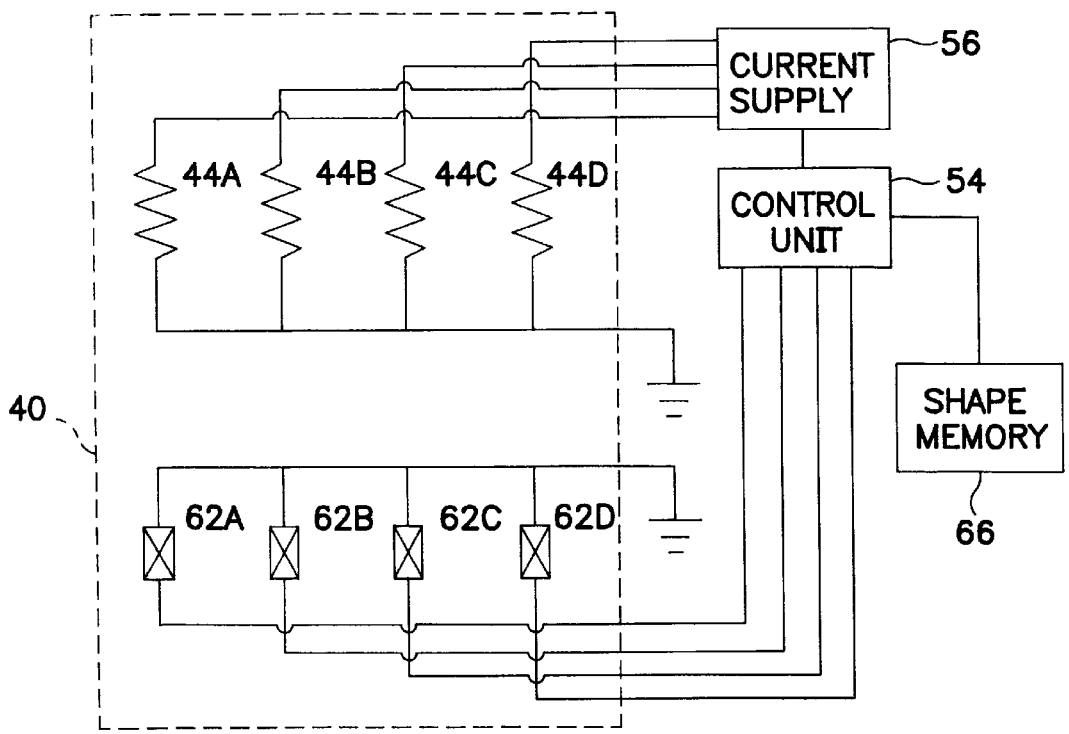
FIG. 13 is a diagram showing the equivalent circuit of an embodiment using deflection sensors.

The electrical diagram with sensors 62 is shown in FIG. 13. The dotted line represents elements mounted on sheet 40. While the connections to elements 44A–44D remain the same, all sensors 62A–62D are wired to control unit 54 via lines 64A–64D respectively. In this manner unit 54 can receive signals representative of the local deflection from each one of sensors 62A–62D individually. A path shape library 66 is connected to control unit 54. Path shape library 66 is capable of mapping the resultant shape of sheet 40 based on information delivered from sensors 62.

Preferably, path shape library 66 has an inventory of resultant shapes produced by known combinations of elements 44. In other words, path shape library 66 is capable of recalling mapped resultant shapes positions and storing new ones. In the most preferred embodiment path shape library 66 can also store the actual current values corresponding to intermediate shapes of adjacent portions. This means that in operation shapes can be recalled and stored at will. The embodiment is thus highly versatile and practical for any diverse applications, e.g., guiding catheters.

Figure 15:
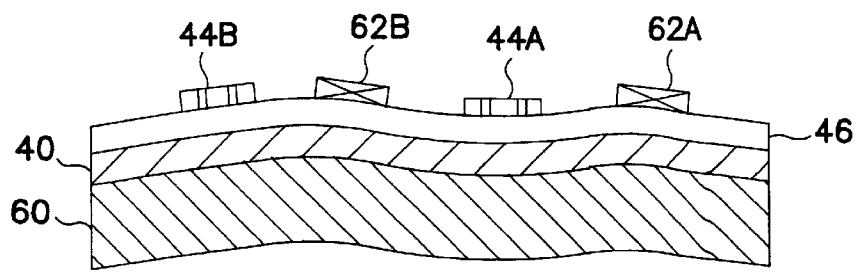
FIG. 15 is a cross sectional view of a two-dimensional sheet with deflection sensors mounted next to heating elements.
Figure 16:
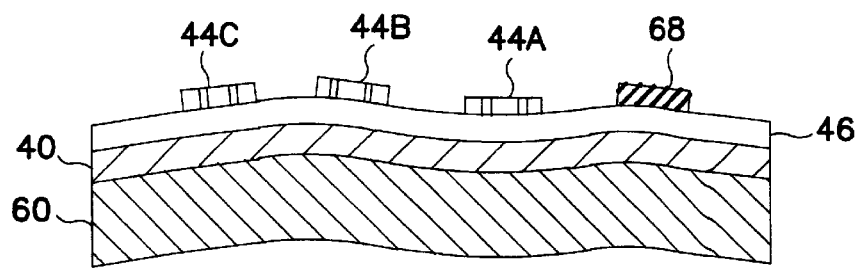
FIG. 16 is a cross sectional view showing a two-dimensional sheet with a temperature sensor.

FIG. 15 shows another embodiment which differs from the above only in that sensors 62 are positioned between elements 44. FIG. 16 shows another modification in which a temperature sensor 68 is mounted between elements 44. This is advantageous for monitoring the temperature of sheet 40. In a particularly preferred embodiment this data is stored in path shape library 66. Checking the temperature form sensor 68 during operation can prevent overheating and other related malfunctions. Of course, more than one thermal sensor 68 can be provided. Ideally, a number of such sensors 68 can be provided. Ideally, a number of such sensors 68 are optimally positioned on sheet 40.

Figure 17:
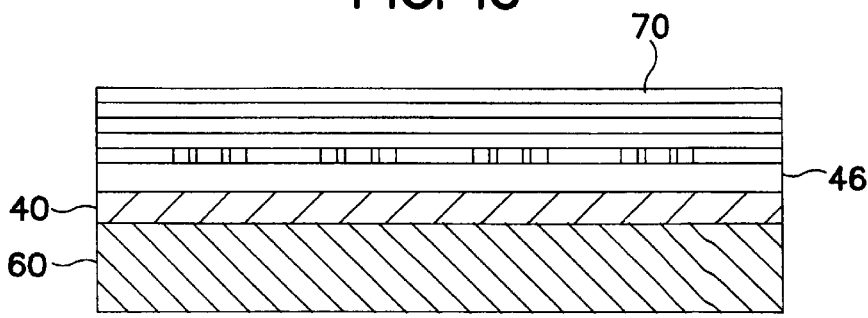
FIG. 17 is a cross sectional view of a two-dimensional sheet with protective coating applied over the eating elements.

FIG. 17 shows the embodiment of FIG. 14 in the martensitic state encapsulated in a top coating layer 70. Layer 70 is applied to protect the electrical connections and elements 44 in particular from damaging environmental factors, e.g., corrosive environments.

Figure 18:
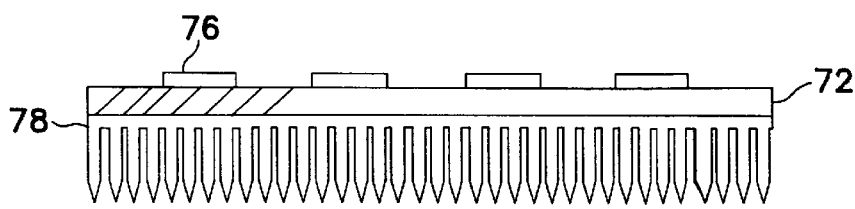
FIG. 18 is a cross section of a two-dimensional sheet using vanes for heat dissipation.
Figure 19:
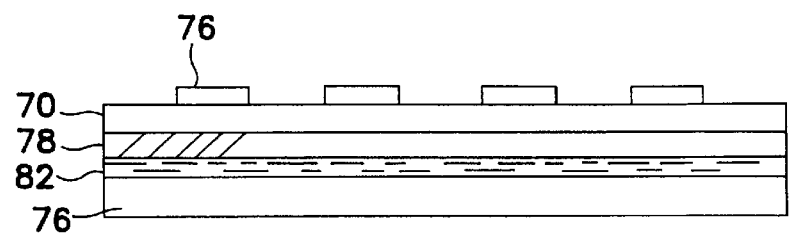
FIG. 19 is a cross section of a two-dimensional sheet using water ducts for heat dissipation.

FIG. 18 and FIG. 19 show two ways in which a two-dimensional sheet 72 of SMA can be cooled. For simplicity, all other elements, except for heating elements 76, have been omitted. In FIG. 18 the cooling element is a set of fins 78 in direct contact with sheet 72. This arrangement ensures efficient heat transfer and dissipation. Similarly, the structure id FIG. 19 efficiently dissipates heat using a substrate layer 80 with ducts 82 (only one shown). Ducts 82 carry a coolant, e.g., water, which absorbs and carries away the waste thermal energy.

As shown in FIG. 20, a two way shape memory effect of sheet 12 is shown with sheet 12 (hereafter "actuator 12") positioned coincident along a catheter 84 axis. Actuator 12 can be made of a shape memory material or a bimorph structure and can formed of a continuous sheet, a discontinuous sheet, a rod, mesh, wire-like structure as well as other three dimensional shapes. It will be appreciated that actuator 12 can also be parallel but adjacent to the catheter axis, as well as positioned on a surface of catheter 84. The two-way shaped memory effect provides for a deflection in two directions and a portion of actuator 12 is strained which provides an internal bias spring force. Actuator 12 then bends one way in its activated state and returns to the opposite direction in its inactivated state. Only a portion of actuator 12 can have a two-way shape.

Referring now to FIG. 21, two single SMA actuators 12 are illustrated. Each actuator 12 operates in a one way shape memory effect. The two actuators 12 are mechanically coupled and thermally insulated from one another. The use of two single actuators 12 in this manner can be used as a stand along guide wire or as a component of a catheter of other medical where guidance is needed.

As illustrated in FIG. 22, actuator 12 is coupled to catheter 84. A plurality of segments 12' are formed from a single actuator 12 and are positioned in an interior of catheter 84, at an exterior surface of catheter 84, or are formed within a catheter body. Additionally, actuator 12 can be a guide wire used with catheter 84.

Actuation of actuator 12 can be in a push or pull mode. The push mode is shown in FIG. 23. If actuator 12 is pushed then an outer jacket is not required. If actuator 12 is pulled, an outer jacket is required. The outer jacket provides thermal insulation and coupling where actuator 12 has a plurality of sections which can be "finger-like segments". When catheter 84 is formed of any material that provides slippage or deformation, and actuator 12 is coupled to such a catheter 84, then a sleeve that provides a low coefficient of friction of actuator 12 with respect to catheter 84, is not required.

Figures 24A, 24C:
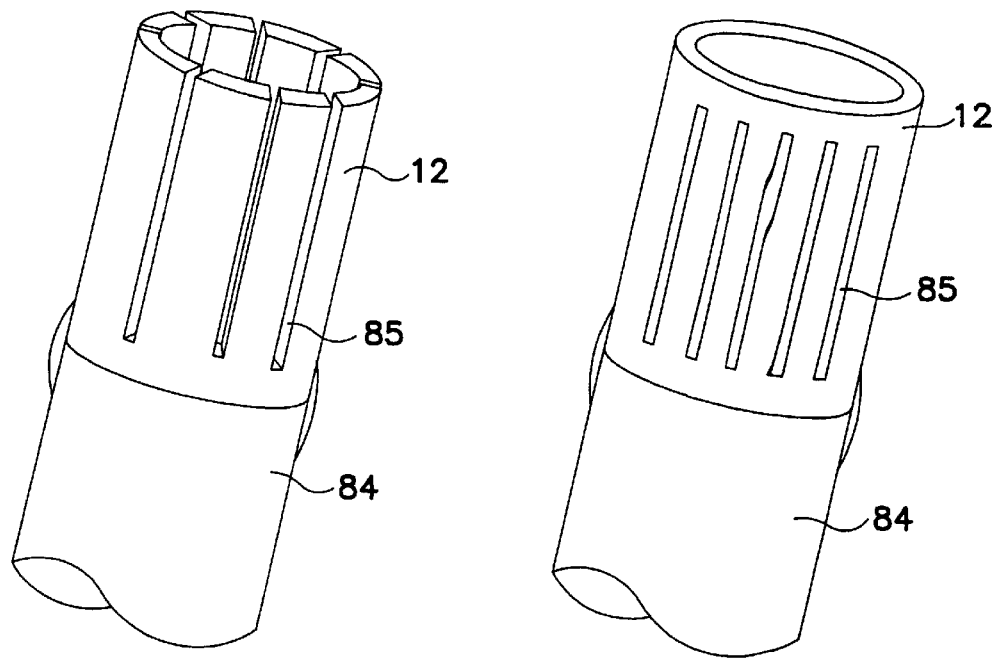
FIG. 24(a) is a perspective view of an actuator of the present invention coupled to the distal end of a catheter and the actuator includes actuator slots that extending to a distal end of the actuator.
FIG. 24(c) is a perspective view of an actuator of the present invention coupled to a distal end of a catheter and the actuator includes slots that do not extend to proximal or distal ends of the actuator.
Figure 24B:
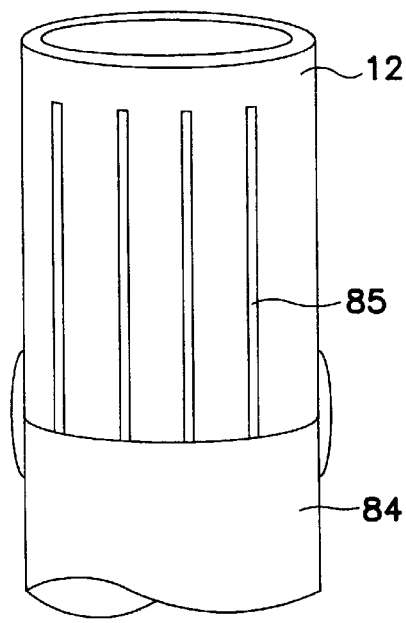
FIG. 24(b) is a perspective view of an actuator of the present invention with the distal ends of "finger-like segments" of actuator 12 joined to the distal end of a catheter.

In FIG. 24(a), actuator 12 is positioned at a distal end of catheter 84. Actuator 12 includes a plurality of finger-like segments that are separated by slots 85 that extend to the distal end of actuator 12. In the embodiment of FIG. 24(a), catheter 84 does not include a core and only a single continuous actuator 12 is provided. The distal end of catheter 84 is capable of attaining complex shapes and bends in multiple planes by selectively applying energy to different sections of actuator 12. In the embodiment illustrated in FIG. 24, actuator 12 includes a proximal end that is joined to catheter 84 by methods well known to those skilled in the art. As shown in FIG. 24(b) the distal ends of the finger-like segments of actuator 12 are joined to the distal end of catheter 84.

Slots 85 in FIGS. 24(a), (b) and (c) are spaced sufficiently close such that the combined maximum lateral and normal surface strain at each finger-like segment does not exceed 10% during lateral bending, and preferably does not exceed 5%. Slots 85 are sufficiently narrow to maximize bending forces of the finger-like segments while permitting lateral strain.

Referring now to FIG. 24(c) actuator 12 includes a plurality of slots 85 which do not extend to the proximal or distal ends of actuator 12. In this embodiment, a separate coupling element is not needed.

Figure 25:
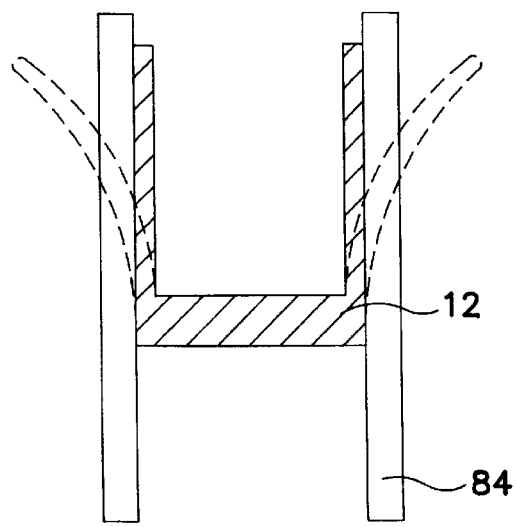
FIG. 25 illustrates the positioning of the actuator of FIG. 2 in an interior of a catheter.
Figure 26:
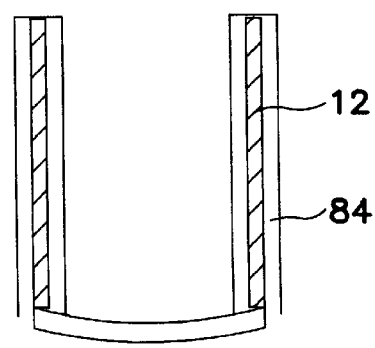
FIG. 26 illustrates the inclusion of the actuator of FIG. 2 in a catheter body.

In FIG. 25, actuator 12 is shown as being positioned in an interior of catheter 84 without an additional coupling device or a core positioned in catheter 84. As illustrated in FIG. 26, actuator 12 is positioned in a body of catheter 84 and may be co-extruded.

Figure 27:
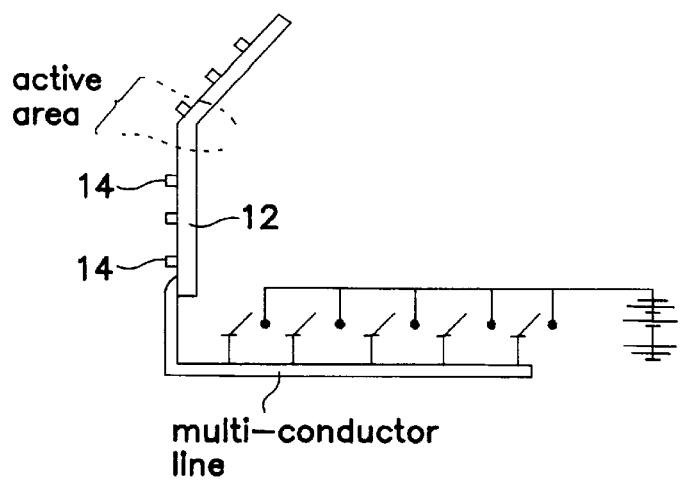
FIG. 27 illustrates the selective heating capability of the actuator of FIG. 2.

Referring now to FIG. 27, only selected sections of actuator 12 are locally heated by selected heating elements and the proximity of heating elements 14 to actuator 12 provide a thermal path whereby energy is transferred by heating elements 14 to one or more sections of actuator 12. Upon activation a section of actuator 12 moves partially of fully to its minimum bend radius imparted to it during its thermal training. In FIG. 28, actuator 12 is shown as being positioned in a lumen-less catheter 84.

As shown in FIG. 29, actuator 12 is a shape memory alloy mesh instead of a solid sheet. In FIG. 30 the mesh configuration is formed in a basket and thermally trained in a crushed configuration. The mesh can be co-extruded with an elastomer 86 which can be the catheter 84 or a separate element. Elastomer 86 can also be cast, heat shrunk, dipped and the like with mesh 12. Elastomer 86 provides the function of a return spring to the one-way action of actuator 12. The one-way spring actuation can also be provided by other mechanical devices, structure and configurations. Thin film heaters 14 are distributed on surfaces of the mesh and provide local heating of the shape memory alloy mesh 12. In FIG. 31, different sections of mesh 12 are activated to varying degrees in order to achieve a desired deflection the elastomer.

Figure 32:
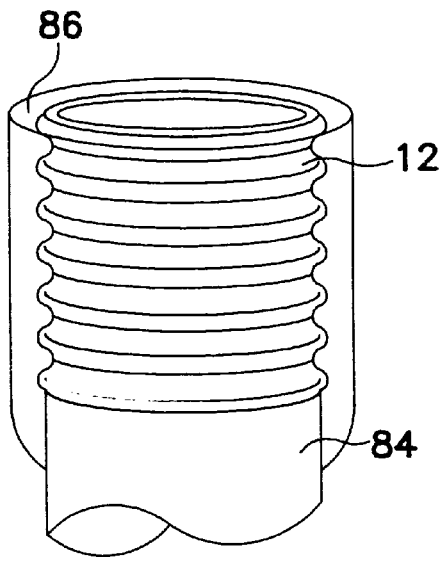
FIG. 32 illustrates a shape memory alloy corrugated tube.
Figure 33:
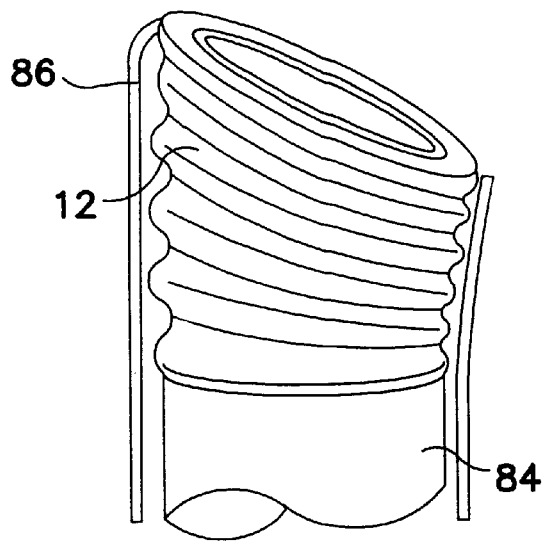
FIG. 33 illustrates the result of applying heat to selected sections of the corrugated tube of FIG. 32.
Figure 34:
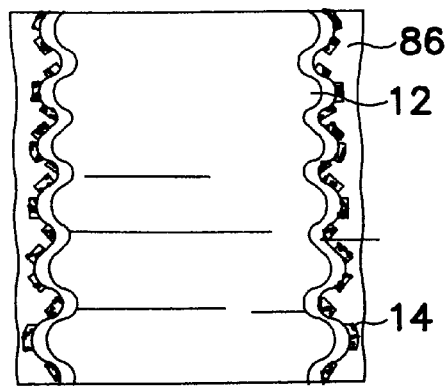
FIG. 34 illustrates a cross-sectional view of the apparatus of FIG. 32.

Referring now to FIG. 32, actuator 12 is a shape memory alloy corrugated tube 12 which provides for large axial contractions. The shape memory alloy corrugated tube 12 can be co-extruded with elastomer 86 which can be the catheter 84 or a separate element. Thin film heater elements 14 are positioned on a surface of the shape memory alloy corrugated tube 12 and provide local heating of the shape memory corrugated tube. In FIG. 33, different sections of the shape memory alloy corrugated tube 12 are activated to varying degrees in order to achieve a desired deflection of the elastomer 86. Referring now to FIG. 34, a cross-sectional view of shape memory alloy corrugated tube 12 is illustrated. Heating elements 14 are positioned on the surface of shape memory alloy corrugated tube 12 and a return spring function is provided by elastomer 86 which can be inside, outside or co-extruded with shape memory alloy corrugated tube 12. Additionally, the return spring function can be provide a super elastic form of shape memory alloy sheet 12 which is mechanically coupled to shape memory alloy corrugated tube 12.

While the invention has been described in connection with what is presently considered to be the most practical and preferred embodiments, it is to be understood that the invention is not limited to the disclosed embodiments, but on the contrary, is intended to cover various modifications and equivalent arrangements included within the spirit and scope of the appended claims. For example, a Peatier device could also provide an equivalent solution to heat dissipation. Therefore, persons of ordinary skill in this field are to understand that all such equivalent structures are to be included within the scope of the following claims.

What is claimed is:

1. A catheter, comprising:
   an elongated device including a distal end, a proximal end, and a longitudinal axis;
   a shape memory alloy member coupled to the elongated device;
   an insulating film positioned on a surface of the shape memory alloy member and electrically isolating the shape memory alloy member from passage of current through the shape memory alloy member; and
   a plurality of independently controllable heating elements patterned on the insulating film, each of the independently controllable heating elements of the plurality providing heat to an adjacent selected section of the shape memory alloy member and providing activation of only an area below the independently controllable heating element of the elongated device in a lateral direction relative to the longitudinal axis of the elongated member.

2. The catheter of claim 1, wherein an activation of at least a portion of the selected section provides a variable Young's modulus of at least a portion of the shape memory alloy member.

3. The catheter of claim 1, further comprising: a microfabricated conductive path coupled to the plurality of independently controllable heating elements.

4. The catheter of claim 1, wherein the member is positioned substantially parallel to the longitudinal axis of the elongated device.

5. The catheter of claim 1, wherein the member is a continuous sheet.

6. The device of claim 1, wherein the member is a sheet which includes perforations.

7. The catheter of claim 1, wherein the shape memory alloy member is made of a plurality of interconnected separate shape memory alloy members.

8. The catheter of claim 1, wherein the shape memory alloy member has a three-dimensional geometry.

9. The device of claim 1, wherein the member is a wire-like structure.

10. The catheter of claim 1, wherein the shape memory alloy member is a tube-like structure.

11. A catheter, comprising:
    an elongated device including a distal end, a proximal end, and a longitudinal axis;
    a shape memory alloy member coupled to the elongated device;
    an insulating film positioned on a surface of the shape memory alloy member and electrically isolating the shape memory alloy member from passage of current through the shape memory alloy member; and
    a plurality of independently controllable heating elements patterned on the insulating film, each of the independently controllable heating elements of the plurality providing heat to an adjacent selected section of the shape memory alloy member and providing activation of only an area below the independently controllable heating element of the elongated device in a lateral direction relative to the longitudinal axis of the elongated member, wherein the shape memory alloy member includes at least one slot formed in the shape memory alloy member.

12. The catheter of claim 1, wherein the member is positioned on an external surface of the elongated device.

13. The catheter of claim 1, wherein the shape memory alloy member is positioned on an internal surface of the elongated device.

14. The catheter of claim 1, wherein the member is positioned on an external surface of the elongated device.

15. The catheter of claim 1, wherein the shape memory alloy member is positioned in an interior section of the elongated device.

16. The catheter of claim 1, wherein the member is positioned at least partially circumferentially around the elongated device.

17. The catheter of claim 1, wherein the member is positioned at least partially circumferentially at an exterior surface of the elongated device.

18. The catheter of claim 1, wherein the shape memory alloy member is positioned at least partially circumferentially at an interior surface of the elongated device.

19. The catheter of claim 1, wherein the shape memory alloy member is positioned at least partially circumferentially in an interior of the elongated device.

20. The catheter of claim 1, wherein the elongated device has a tubular geometric configuration.

21. The catheter of claim 1, wherein the elongated device has a solid cross-section.

22. The catheter of claim 1, wherein the elongated device includes an interior lumen.

23. A catheter, comprising: a shape memory alloy member with a longitudinal axis and configured to be selectively activated at a selected site of the shape memory alloy member;

an insulating film positioned on a surface of the shape memory alloy member and electrically isolating the shape memory alloy member from passage of current through the shape memory alloy member; and a plurality of independently controllable heating elements patterned on the insulating film, each of the independently controllable heating elements of the plurality providing heat to an adjacent selected section of the shape memory alloy member and providing activation of only an area below the independently controllable heating element of the adjacent selected section in a lateral direction relative to the longitudinal axis of the sheet of the shape memory alloy member.

24. The catheter of claim 23, wherein an activation of at least a portion of the selected section provides a variable Young's modulus of at least a portion of the shape memory alloy member.

25. The catheter of claim 23, further comprising:

a micro-fabricated conductive path coupled to the plurality of independently controllable heating elements.

26. A catheter, comprising: a shape memory alloy member with a longitudinal axis and configured to be selectively activated at a selected site of the shape memory alloy member;

an insulating film positioned on a surface of the shape memory alloy member and electrically isolating the shape memory alloy member from passage of current through the shape memory alloy member; and a plurality of independently controllable heating elements patterned on the insulating film, each of the independently controllable heating elements of the plurality providing heat to an adjacent selected section of the shape memory alloy member and providing activation of only an area below the independently controllable heating element of the adjacent selected section in a lateral direction relative to the longitudinal axis of the sheet of the shape memory alloy member; and a plurality of patterned conductor lines, each of the patterned conductor lines being coupled to an independently controllable heating element, the plurality of conductor lines being patterned on the insulating film.

27. The catheter of claim 23, wherein the shape memory alloy member is made of a plurality of interconnected separate shape memory alloy members.

28. The catheter of claim 23, wherein the shape memory alloy member includes at least one slot formed in the shape memory alloy member.

29. A catheter, comprising:

an elongated device including a distal end, a proximal end, and a longitudinal axis;

a shape memory alloy member coupled to the elongated device;

an insulating film positioned on a surface of the shape memory alloy member and electrically isolating the shape memory alloy member from passage of current through the shape memory alloy member; and a plurality of independently controllable heating elements patterned on the insulating film, each of the independently controllable heating elements of the plurality providing heat to an adjacent selected section of the shape memory alloy member and providing activation of only an area below the independently controllable heating element of the elongated device in a lateral direction relative to the longitudinal axis of the elongated member; and a plurality of conductor lines, each of the conductor lines being coupled to an independently controllable heating element, the plurality of conductor lines being patterned on the insulating film.

* * * * *